United States Patent [19]

Nita et al.

[11] Patent Number: 5,417,672

[45] Date of Patent: May 23, 1995

[54] CONNECTOR FOR COUPLING AN ULTRASOUND TRANSDUCER TO AN ULTRASOUND CATHETER

[75] Inventors: Henry Nita, Mission Viejo; Martinos Tran, Garden Grove; Douglas H. Gesswein, Mission Viejo; Timothy C. Mills, Newport Beach, all of Calif.

[73] Assignee: Baxter International Inc., Deerfield, Ill.

[21] Appl. No.: 131,065

[22] Filed: Oct. 4, 1993

[51] Int. Cl.$^6$ .............................................. A61M 25/00
[52] U.S. Cl. ........................................ 604/283; 601/2; 606/169
[58] Field of Search ......................... 604/22, 283, 905; 601/2; 606/169, 171

[56] References Cited

U.S. PATENT DOCUMENTS

| | | |
|---|---|---|
| 3,352,303 | 11/1967 | Delaney . |
| 3,433,226 | 3/1969 | Boyd . |
| 3,526,219 | 9/1970 | Balamuth . |
| 3,565,062 | 3/1971 | Kuris . |
| 3,589,363 | 6/1971 | Banko . |
| 3,618,594 | 11/1971 | Banko . |
| 3,809,093 | 5/1974 | Abraham . |
| 3,823,717 | 7/1974 | Pohlman . |
| 3,861,391 | 1/1975 | Antonevich et al. . |
| 3,896,811 | 7/1975 | Storz . |
| 4,188,952 | 2/1980 | Loschivlov et al. . |
| 4,214,586 | 7/1980 | Mericle . |
| 4,223,676 | 9/1980 | Wuchinich et al. . |
| 4,337,090 | 6/1982 | Harrison . |
| 4,366,819 | 1/1983 | Kaster . |
| 4,431,006 | 2/1984 | Trimmer et al. . |
| 4,474,180 | 10/1984 | Angulo . |
| 4,505,767 | 3/1985 | Quin . |
| 4,565,589 | 1/1986 | Harrison . |
| 4,587,958 | 5/1986 | Noguchi et al. . |
| 4,587,972 | 5/1986 | Morantte . |
| 4,589,419 | 5/1986 | Laughlin et al. . |
| 4,665,906 | 5/1987 | Jervis . |
| 4,692,139 | 9/1987 | Stiles . |
| 4,741,731 | 5/1988 | Starck et al. ......................... 601/2 |
| 4,750,902 | 6/1988 | Wuchinich et al. . |
| 4,764,165 | 8/1988 | Reimels et al. ...................... 604/22 |
| 4,794,931 | 1/1989 | Yock . |
| 4,799,496 | 1/1989 | Hargraves . |
| 4,800,876 | 1/1989 | Fox et al. . |
| 4,808,153 | 2/1989 | Parisi . |
| 4,811,743 | 3/1989 | Stevens . |
| 4,821,731 | 4/1989 | Martinelli et al. . |
| 4,841,977 | 6/1989 | Griffith . |
| 4,844,092 | 7/1989 | Rydell . |
| 4,867,141 | 9/1989 | Nakada . |

(List continued on next page.)

FOREIGN PATENT DOCUMENTS 1531659 7/1977 European Pat. Off. .

(List continued on next page.)

OTHER PUBLICATIONS

Circulation, vol. 81, No. 2, Feb. 1990, "Application of a New Phased-Array Ultrasound Imaging Catheter in the Assessment of Vascular Dimensions," pp. 660–666.

"Ultrasonic Energy Causes Doe-Dependent, Endothelium-Independent Arterial Relaxation"–T. Fischell, et al. Abstracts of the 63rd Scientific Sessions, p. III--219.

Primary Examiner—C. Fred Rosenbaum
Assistant Examiner—Frank Wilkens, III
Attorney, Agent, or Firm—Stetina Brunda & Buyan; Raymond Sun

[57] ABSTRACT

A connector for attaching an ultrasound transducer to an ultrasound catheter has a support member formed on the ultrasound transducer for supporting at least a portion of a catheter coupling which is disposed at the proximal end of ultrasound catheter. The support member preferably comprises a collar slideably disposed upon the ultrasound transducer so as to move from a non-supporting position wherein the collar is disposed adjacent the catheter coupling to a supporting position wherein the collar is disposed around and engages the catheter coupling. Supporting at least a portion of the catheter coupling mitigates the occurrence of ultrasound transmission member breakage by reducing mechanical stress applied to the proximal end thereof.

22 Claims, 4 Drawing Sheets

U.S. PATENT DOCUMENTS

| | | |
|---|---|---|
| 4,870,953 | 10/1989 | DonMichael . |
| 4,898,575 | 2/1990 | Fischell et al. . |
| 4,917,097 | 4/1990 | Proudian et al. . |
| 4,919,133 | 4/1990 | Chiang . |
| 4,920,954 | 5/1990 | Alliger et al. . |
| 4,923,441 | 5/1990 | Shuler . |
| 4,924,863 | 5/1990 | Sterzer . |
| 4,936,281 | 6/1990 | Stasz . |
| 4,957,111 | 9/1990 | Millar . |
| 4,960,411 | 10/1990 | Buchbinder . |
| 4,966,583 | 10/1990 | Debbas . |
| 4,967,653 | 11/1990 | Hinz . |
| 4,967,753 | 11/1990 | Haase et al. . |
| 4,979,939 | 12/1990 | Shiber . |
| 4,988,356 | 1/1991 | Crittenden . |
| 4,989,583 | 2/1991 | Hood ................ 601/2 |
| 4,998,527 | 3/1991 | Meyer . |
| 5,022,399 | 6/1991 | Biegeleisen . |
| 5,029,588 | 7/1991 | Yock et al. . |
| 5,058,570 | 10/1991 | Idemoto et al. . |
| 5,061,238 | 10/1991 | Shuler . |
| 5,069,664 | 12/1991 | Guess et al. . |
| 5,076,276 | 12/1991 | Sakurai et al. . |
| 5,100,423 | 3/1992 | Fearnot . |
| 5,151,085 | 9/1992 | Sakurai . |
| 5,163,421 | 11/1992 | Bernstein . |
| 5,188,589 | 2/1993 | Wyoych et al. ............ 604/22 |
| 5,199,943 | 4/1993 | Wyoych ............... 604/22 |
| 5,211,625 | 5/1993 | Sakurai . |
| 5,242,385 | 9/1993 | Strukel ................ 604/22 |
| 5,248,296 | 9/1993 | Alliger . |
| 5,255,669 | 10/1993 | Kubota . |
| 5,261,877 | 11/1993 | Fine et al. ............... 604/22 |
| 5,267,954 | 12/1993 | Nita . |
| 5,269,297 | 12/1993 | Weng . |
| 5,312,328 | 5/1994 | Nita et al. ............... 604/22 |

FOREIGN PATENT DOCUMENTS

| | | |
|---|---|---|
| 0424231 | 4/1984 | European Pat. Off. . |
| 189329 | 7/1986 | European Pat. Off. . |
| 293472 | 11/1986 | European Pat. Off. . |
| 208175 | 1/1987 | European Pat. Off. . |
| 0209468 | 1/1987 | European Pat. Off. . |
| 234951 | 2/1987 | European Pat. Off. . |
| 347098 | 6/1988 | European Pat. Off. . |
| 316796 | 11/1988 | European Pat. Off. . |
| 315290 | 10/1989 | European Pat. Off. . |
| 443256 | 12/1990 | European Pat. Off. . |
| 472368 | 2/1992 | European Pat. Off. . |
| 2424733 | 11/1980 | France . |
| 2641693 | 7/1990 | France . |
| 2643272 | 8/1990 | France . |
| 2349120 | 4/1975 | Germany . |
| 2438648 | 2/1976 | Germany . |
| 2453058 | 5/1976 | Germany . |
| 2453126 | 5/1976 | Germany . |
| 2541919 | 3/1977 | Germany . |
| 2703486 | 12/1977 | Germany . |
| 3726210 | 8/1987 | Germany . |
| 3707567 | 9/1987 | Germany . |
| 3707921 | 9/1987 | Germany . |
| 3826414 | 2/1989 | Germany . |
| 3812836 | 4/1990 | Germany . |
| 1520448 | 10/1975 | United Kingdom . |
| 2208138A | 3/1989 | United Kingdom . |
| 2212267 | 7/1989 | United Kingdom . |
| WO87/01276 | 3/1987 | WIPO . |
| WO87/05793 | 10/1987 | WIPO . |
| WO89/05123 | 6/1989 | WIPO . |
| WO89/06515 | 7/1989 | WIPO . |
| WO89/07419 | 8/1989 | WIPO . |
| WO90/01300 | 2/1990 | WIPO . |
| WO90/07303 | 7/1990 | WIPO . |
| WO91/02489 | 3/1991 | WIPO . |
| WO91/14401 | 10/1991 | WIPO . |
| WO92/10140 | 6/1992 | WIPO . |
| WO92/11815 | 7/1992 | WIPO . |
| WO92/15253 | 9/1992 | WIPO . |

CONNECTOR FOR COUPLING AN ULTRASOUND TRANSDUCER TO AN ULTRASOUND CATHETER

FIELD OF THE INVENTION

The present invention relates generally to medical devices and more particularly to a device and method for attaching an ultrasound catheter to an ultrasound transducer such that the occurrence of ultrasound transmission member breakage is mitigated by reducing mechanical stress applied to the proximal end thereof.

BACKGROUND OF THE INVENTION

A number of ultrasonic devices have heretofore been proposed for use in ablating or removing obstructive material from blood vessels. Examples of devices which purportedly utilize ultrasonic energy, alone or in conjunction with other treatment modalities, to remove obstructions from blood vessels include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al.), 4,920,954 (Alliger, et al.), and 5,100,423 (Fearnot) as well as other patent publications W087-05739 (Cooper), W089-06515 (Bernstein, et al.), W090-0130 (Sonic Needle Corp.), EP316789 (Don Michael, et al.), DE3,821,836 (Schubert) and DE2,438,648 (Pohlman).

Ultrasound transmitting catheters have been utilized to successfully ablate various types of obstructions from blood vessels of humans and animals. Particular success has been observed in ablation of obstructions located in peripheral blood vessels such as the femoral arteries. Successful applications of ultrasonic energy to smaller blood vessels, such as the coronary arteries, necessitates the use of relatively small diameter ultrasound transmitting catheters which are sufficiently small and flexible to undergo transluminal advancement through the tortuous vasculature of the aortic arch and coronary tree. Because of its small diameter, the ultrasound transmission member which extends through such catheters is particularly susceptible to breakage.

Additionally, ultrasound transmitting catheters may be utilized to deliver ultrasonic energy to blood vessel walls for the purpose of preventing or reversing vasospasm as described in copending U.S. patent application Ser. No. 07/911,651, entitled ANGIOPLASTY AND ABLATIVE DEVICES HAVING ONBOARD ULTRASOUND COMPONENTS AND DEVICES AND METHODS FOR UTILIZING ULTRASOUND TO TREAT OR PREVENT VASOSPASM. The ultrasound transmission member of such catheters are also susceptible to breakage.

As those skilled in the art will appreciate, breakage of ultrasound transmission members typically occurs near the proximal end thereof, generally within a few ultrasound nodes of the interface of the ultrasound catheter coupling and the ultrasound transducer coupling. This is believed to be because energy concentrations are highest at these points. Thus, any external forces applied to the ultrasound transmission member in this region may result in stresses exceeding the elastic limit of the ultrasound transmission member.

External forces may be inadvertently and undesirably applied to the ultrasound transmission member by pressing upon or bumping the ultrasound transmission member coupling during use of the ultrasound catheter. Such pressing upon or bumping of the ultrasound catheter coupling results in bending or other movement thereof which causes the inner wall thereof to contact the ultrasound transmission member. Such contacting of the ultrasound transmission member by the inner wall of the ultrasound catheter coupling applies forces, i.e., frictional and/or bending, thereto. If ultrasound energy is being transmitted by the ultrasound transmission member at the instant such forces are applied thereto, stresses occur which commonly result in breakage of the ultrasound transmission member.

As such, it would be beneficial to provide a means for mitigating the occurrence of ultrasound transmission member breakage by reducing mechanical stress applied to the proximal end of the ultrasound transmission member during operation.

SUMMARY OF THE INVENTION

The present invention specifically addresses and alleviates the above-mentioned deficiencies associated with the prior art. More particularly, the present invention comprises a connector for attaching an ultrasound transducer to an ultrasound catheter, the ultrasound catheter having a transducer coupling formed upon the distal end thereof and the ultrasound catheter having a catheter coupling formed upon the proximal end thereof and an ultrasound transmission member disposed therein. The catheter coupling is typically threaded to the complimentary transducer coupling. The connector comprises a support member formed on the ultrasound transducer for supporting at least a portion of the catheter coupling. Supporting at least a portion of the catheter coupling mitigates the occurrence of ultrasound transmission member breakage by reducing mechanical stress applied to the proximal end thereof.

The support member preferably comprises a collar attached to the ultrasound transducer and disposed about at least a portion of the catheter coupling. The collar is preferably slideably disposed upon the ultrasound transducer and thus has a non-supporting or first position wherein the collar is disposed adjacent the catheter coupling and a supporting or second position wherein the collar is disposed around at least a portion of the catheter coupling so as to provide support thereto.

The collar preferably comprises a plurality of open ended slots formed therein so as to define a plurality of gripping fingers. The gripping fingers firmly engage and grip the catheter coupling when the collar is disposed in the second position thereof.

The collar preferably further comprises at least one close-ended slot formed therein and a pin rigidly attached to the ultrasound transducer such that the pin extends through the close-ended slot, thereby limiting proximal and distal movement of the collar so as to define the first and second positions thereof.

The collar preferably further comprises a tapered bore for receiving the catheter coupling. The tapered bore more tightly grips the catheter coupling as the collar is moved from the first position thereof toward the second position thereof. Thus, as the catheter coupling is received deeper into the tapered bore of the collar, the collar tightens upon the catheter coupling so as to better grip the catheter coupling.

The collar preferably further comprises a counter sink at the opening of the tapered bore for facilitating movement from the first position to the second position thereof. The counter sink allows the catheter coupling to be more easily and smoothly received within the tapered bore of the collar.

These, as well as other advantages of the present invention will be more apparent from the following description and drawings. It is understood that changes in the specific structure shown and described may be made within the scope of the claims without departing from the spirit of the invention.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The connector for attaching an ultrasound transducer to an ultrasound catheter of the present invention is illustrated in FIGS. 1–9 which depict a presently preferred embodiment of the invention.

Figures 1, 2:
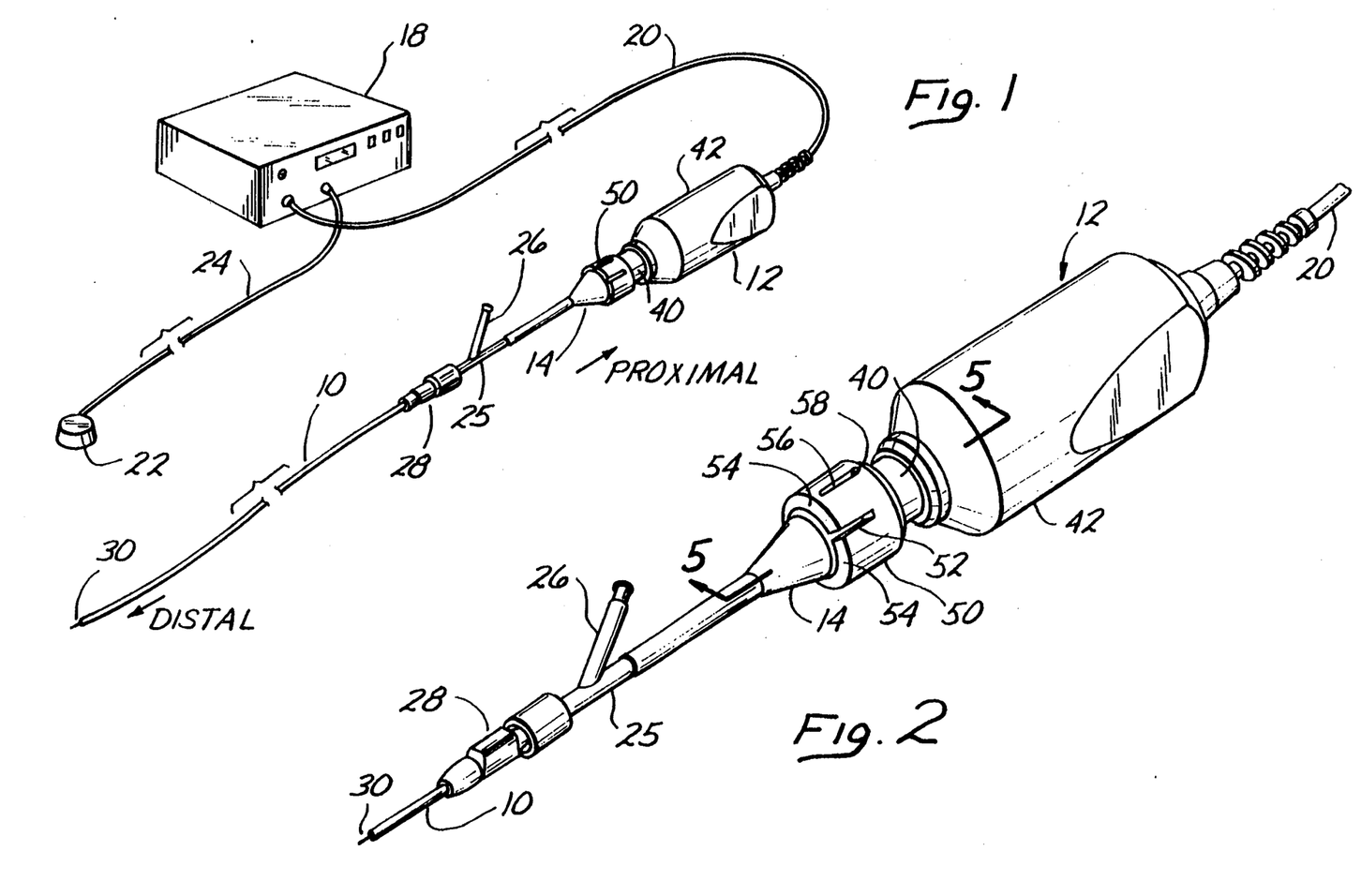
FIG. 1 is a perspective view of an ultrasound catheter attached to an ultrasound transducer utilizing an improved connector therefor according to the present invention.
FIG. 2 is an enlarged perspective view of the proximal end of the ultrasound catheter and the distal end of the ultrasound transducer of FIG. 1 showing attachment of the catheter coupling to the transducer coupling.
Figure 3:
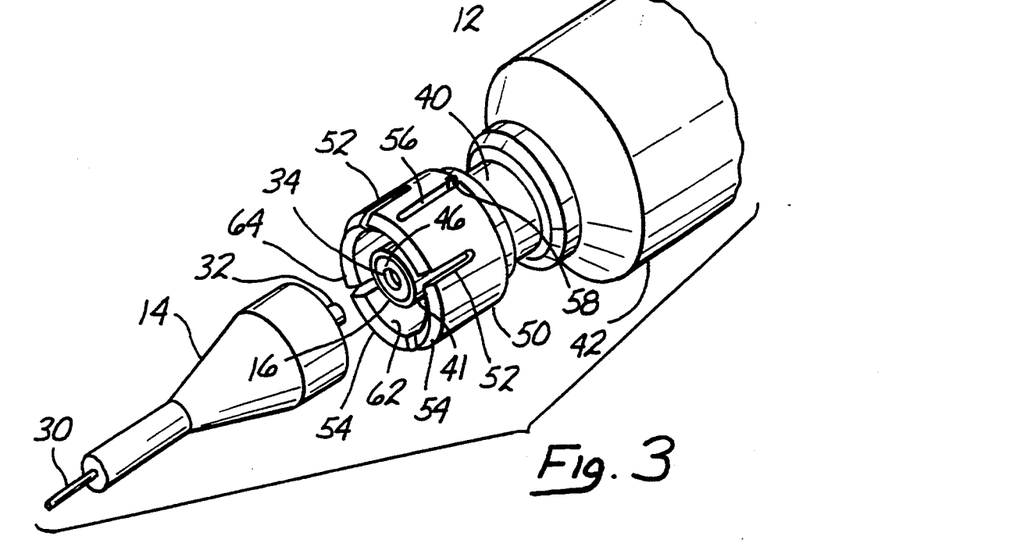
FIG. 3 is an enlarged perspective view of the catheter coupling and transducer coupling of FIG. 2 showing the catheter coupling and the transducer coupling in an uncoupled configuration.

Referring now to FIGS. 1–3, an ultrasound catheter 10 is attached to an ultrasound transducer 12 via a catheter coupling 14 formed at the proximal end of the catheter 10 and a transducer coupling 16 formed at the distal end of the ultrasound transducer 12. The ultrasound transducer 12 is electrically interconnected to signal generator and control electronics 18 via cable 20. The signal generator and control electronics is connected to a foot switch 22 via cable 24.

Catheter connector 14 preferably comprises a Y-joint 25 which facilitates the introduction of various radiopaque dyes and/or medications through connector 26 during therapeutic procedures. The catheter connector 14 attaches to the catheter 10 via catheter connector coupling 28. An ultrasound transmission member 30 extends through the ultrasound catheter 10 and transmits ultrasound energy from the ultrasound transducer 12 to the stenosis or other anatomical site where ultrasound energy is to be applied.

Figures 4, 5:
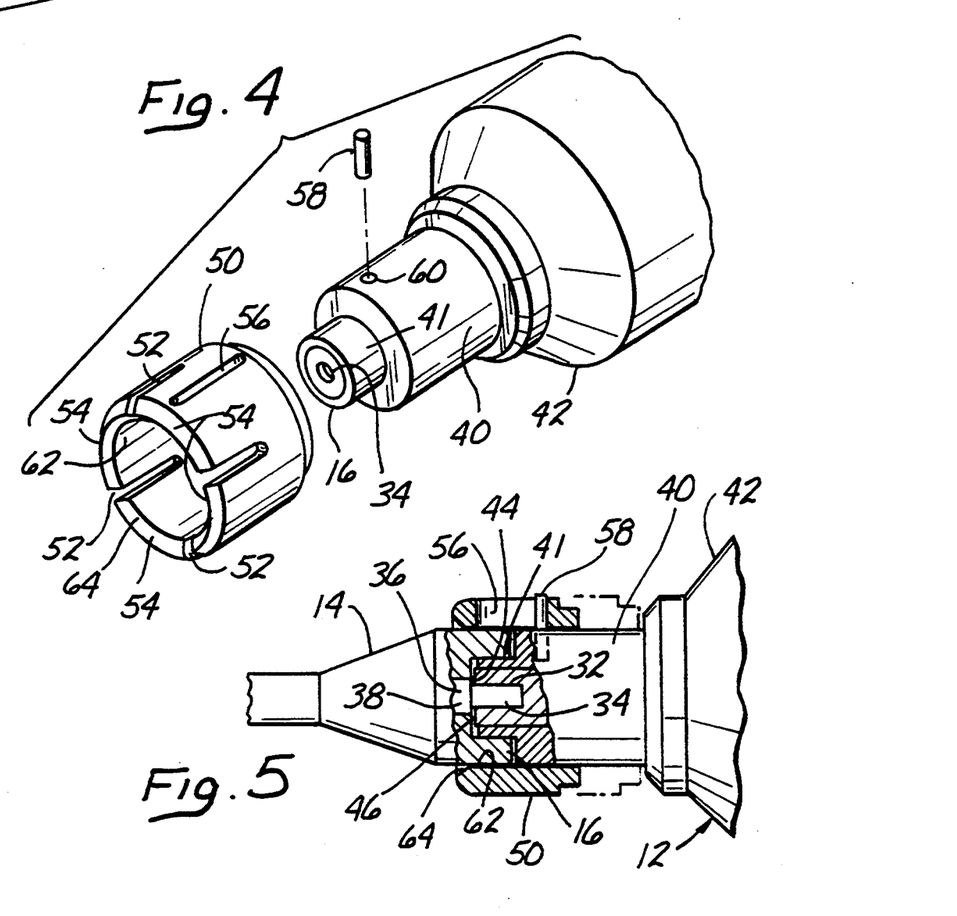
FIG. 4 is an exploded and enlarged perspective view of the transducer coupling of FIG. 3 showing the collar and pin removed from the neck of the ultrasound transducer.
FIG. 5 is a side view, partially in cross-section, of the catheter coupling attached to the transducer coupling.
Figure 6:
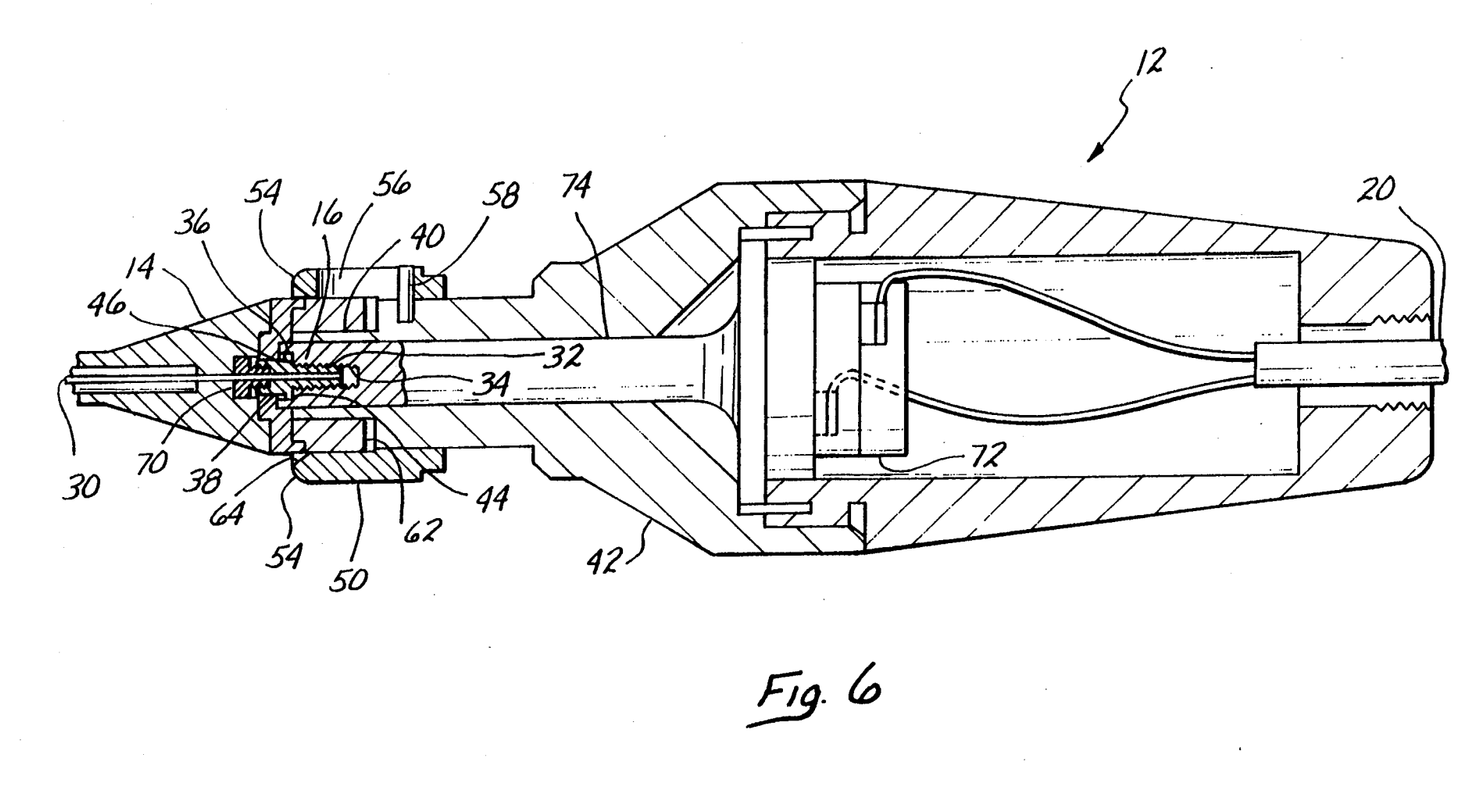
FIG. 6 is an enlarged cross-sectional sideview of the catheter coupling attached to the transducer coupling and also showing the ultrasound transducer element and bell.
Figures 7, 8:
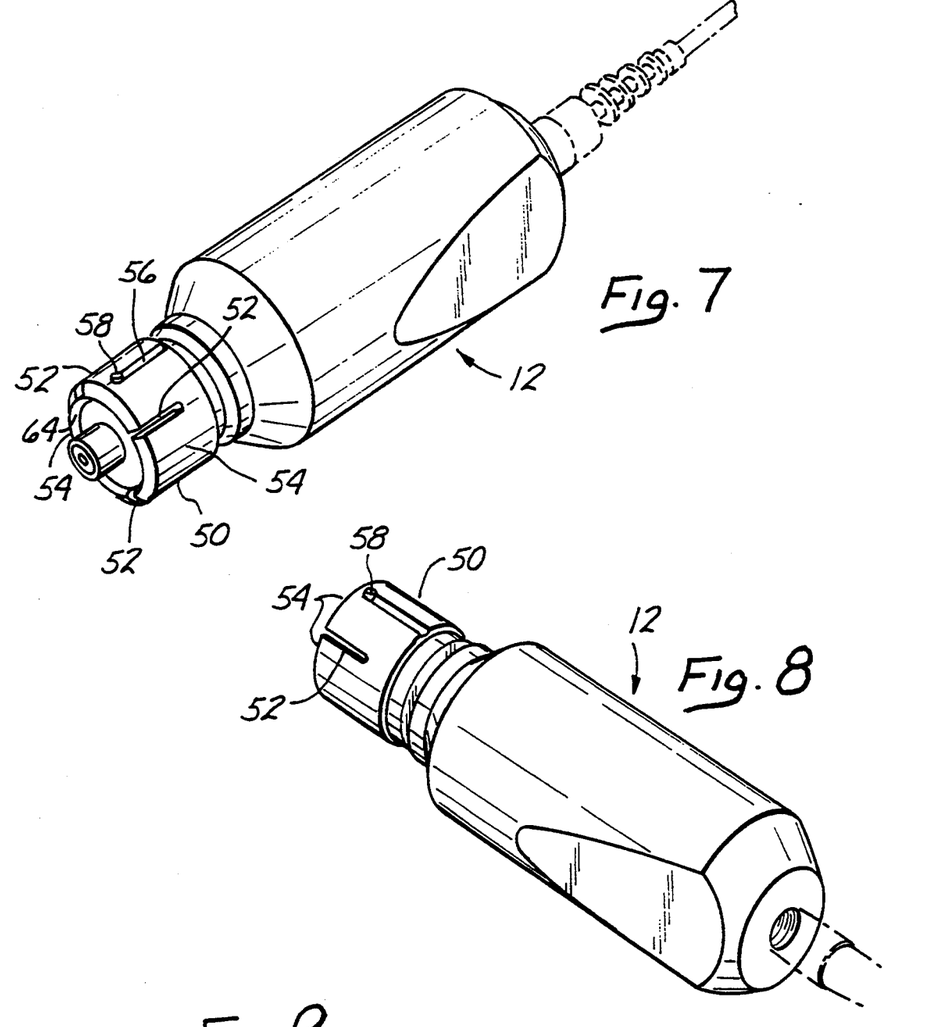
FIG. 7 is a perspective view of the design of the ultrasound transducer of FIGS. 1–6 wherein the opposite side is substantially identical to the side illustrated.
FIG. 8 is a perspective view of the design of FIG. 7 rotated approximately 90° about a vertical axis.
Figure 9:
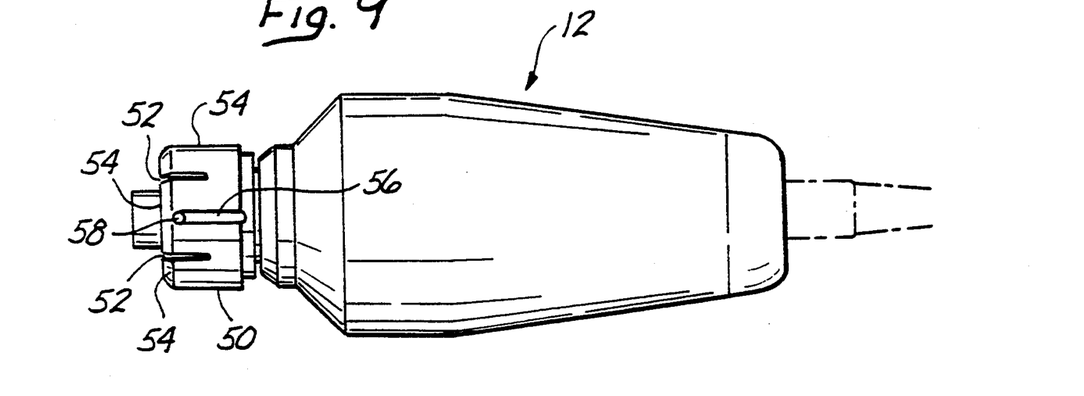
FIG. 9 is a top plan view of the design of FIGS. 7 and 8 wherein the bottom is substantially identical thereto with the exception that the pin and slot formed in the collar are optionally formed upon the bottom thereof.

With particular reference to FIG. 3, the catheter coupling 14 preferably attaches to the transducer coupling 16 by threading threaded male member 32 of the catheter coupling 14 into threaded female member 34 of the transducer coupling 16, such that an abutment surface 44 of the ultrasound transmission member 30 intimately contacts or abuts a complimentary abutment surface 46 of the transducer coupling 16 (as best shown in FIGS. 5 and 6).

The ultrasound transducer coupling 16 is partially defined by boss 41 which extends from the body 42. As those skilled in the art will recognize, the threaded male coupling 32 of the catheter coupling 14 typically comprises a square base 36 (FIGS. 5 and 6) which is slideably disposed within a complimentary square opening 38 within the catheter coupling 14 so as to facilitate longitudinal movement thereof, i.e., ultrasound energy transmission, while also permitting threading of the male member 32 into the female member 34.

The transducer element 72 is attached to the proximal end of the bell 74. The transducer coupling 16 is formed upon the distal end of the bell 74.

The ultrasound transducer 12 preferably comprises a neck 40 formed upon the body 42 thereof, the neck 40 having a reduced diameter as compared to the body 42 of the ultrasound transducer 12.

Referring now to FIGS. 4–6, a collar 50 is slideably disposed around the neck 40 of the ultrasound transducer 12. The collar 50 has a non-supporting or first position wherein the collar 50 is retracted toward the body 42 of the ultrasound transducer 12 and has a supporting second position wherein the collar 50 is extended to engage at least a portion of the catheter coupling 14 of the ultrasound catheter 10.

The collar 50 preferably comprises a plurality of open-ended slots 52 formed therein so as to define a plurality of gripping fingers 54, the gripping fingers firmly gripping the catheter coupling 14 when the collar 50 is disposed in the second position thereof.

A single close ended slot 56 is formed in the collar 50 and a pin 58 is disposed partially within aperture 60 formed in the neck 40 of the ultrasound transducer 12 and extends therefrom and into close ended slot 56 of the collar 50 so as to limit the movement of the collar 50 and to define the first and second positions thereof. The pin 58 thus retains the collar 50 upon the neck 40 of the ultrasound transducer 12. Those skilled in the art will recognize that various other means for retaining the collar 50 upon the neck 40 of the ultrasound transducer 12 are likewise suitable.

The collar 50 is preferably formed to have a tapered bore 62 for receiving the catheter coupling 14 in a manner which more tightly grips the catheter coupling 14 as the collar 50 is moved from the first position thereof toward the second position thereof. A counter sink 64 is formed about the periphery of the opening of the tapered bore 62 so as to facilitate easy entry of the catheter coupling 14 into the tapered bore 62 of the collar 50.

The collar 50 thus forms a support member disposed upon the ultrasound transducer 12 for supporting at least a portion of the catheter coupling 14. Supporting of at least a portion of the catheter coupling 14 mitigates the occurrence of ultrasound transmission member 30 breakage by reducing mechanical stress applied to the proximal end thereof, particularly during use thereof, i.e., during the application of ultrasound energy. The collar 50 tends to mitigate or prevent the transmission of forces, caused by pushing or bumping the catheter coupling 14, from the catheter coupling 14 to the proximal end of the ultrasound transmission member 30 extending therethrough.

Having described the structure of the improved connector for coupling an ultrasound transducer to an ultrasound catheter of the present invention, a brief description of the use thereof may be beneficial. To use the improved connector for coupling an ultrasound transducer to an ultrasound catheter, the catheter coupling 14 is first attached to the transducer coupling 16 according to contemporary practice, i.e., typically via threading one of the two connectors onto the other. Next, the collar 50, which is disposed in its first position during attachment of the catheter coupling 14 to the transducer coupling 16, is moved from the first position thereof to the second position thereof such that a portion of the catheter coupling 14 is received within the tapered bore 62 of the collar 50. As the collar 50 is extended away from the body 42 of the ultrasound transducer 12, the pin 58 disposed within the close ended slot 56 abuts the proximal end of the close ended slot 56, thereby limiting extension of the collar 50 and defining the second position thereof.

The fingers 54 defined by the open ended slot 52 of the collar 50 tightly grip and firmly engage the captured portion of the catheter coupling 14 so as to provide substantial support thereto, thus, mitigating the transfer of stress causing forces therethrough and to the ultrasound transmission member 30. Upon completion of the therapeutic procedure, the ultrasound catheter 10 is removed from the ultrasound transducer 12 by reversing the above procedure, i.e., by retracting the collar 50 and detaching the catheter coupling 14 from the transducer coupling 16.

Those skilled in the art will recognize that various detente means may optionally be formed upon the collar, the ultrasound transducer 12, and/or the catheter coupling 14 so as to snap or temporarily lock the collar 50 into its second position.

It is understood that the exemplary improved connector for coupling an ultrasound transducer to an ultrasound catheter of the present invention described herein and shown in the drawings represents only a presently preferred embodiment thereof. Various modifications and additions may be made to such embodiment without departing from the spirit and scope of the invention. For example, the support member need not be configured as an annular ring or collar, but rather various configurations thereof are contemplated. For example, the support member may be square, triangular, oval, hexagonal, octagonal, etc. Indeed, the support member need not even be generally annular in configuration, but rather may comprise an elongate member or plurality of elongate members which are movably attached to the ultrasound transducer 12 and which engage the catheter coupling 14 in at least one position thereof. Additionally, attachment of the catheter coupling 14 to the transducer coupling 16 need not be via threaded engagement, but rather, those skilled in the art will recognize that various other such means of attachment are likewise suitable. Thus, these and other modifications and additions may be obvious to those skilled in the art and may be implemented to adapt the present invention for use in a variety of different applications.

What is claimed is:

1. A connector for connecting an ultrasound transducer to an ultrasound catheter having an ultrasound transmitting member extending longitudinally therethrough, said connector comprising:
   a) an ultrasound transducer having a transducer coupling;
   b) a catheter coupling formed on said ultrasound transducer for coupling said ultrasound transducer to said catheter at a connection such that ultrasound will be transmitted from said transducer through said ultrasound transmitting member of said catheter;
   c) an annular collar on said transducer for supporting said connection between said transducer coupling and said catheter, wherein said collar is slideably moveable between:
      i) a first non-supporting position whereat said collar is adjacent said connection; and,
      ii) a second supporting position whereat said collar is disposed around said connection to provide support thereto; and
   d) wherein said collar has a plurality of open ended slots formed therein to define a plurality of gripping fingers, said gripping fingers being configured and positioned to firmly engage said catheter when said catheter is coupled to said transducer and when said collar is disposed in said second supporting position.

2. The connector of claim 1 wherein said collar has a tapered internal bore, said tapered internal bore being configured relative to said catheter such that said collar will exert an increasingly strong grip on said catheter as said catheter is moved from said first position to said second position.

3. The connector of claim 1 wherein said collar has a countersink formed therein to facilitate movement from said first position to said second position.

4. The connector of claim 1 wherein said support member is configured to surround and support a proximal portion of said catheter when said catheter is coupled to said transducer.

5. The connector of claim 1 wherein said catheter coupling is threaded to said transducer coupling.

6. The connector of claim 1 wherein said collar comprises an elongate slot formed in said collar, said elongate slot having a closed proximal end; and a pin attached to said transducer and extending into said elongate slot such that abutment of said pin against the proximal end of said elongate slot will limit movement of said collar in the distal direction.

7. A connector for connecting an ultrasound transducer to an ultrasound catheter having an ultrasound transmitting member extending longitudinally therethrough, said connector comprising:
   a) an ultrasound transducer having a transducer coupling;
   b) a catheter coupling formed on said ultrasound transducer for coupling said ultrasound transducer to said catheter at a connection such that ultrasound will be transmitted from said transducer through said ultrasound transmitting member of said catheter;

c) an annular collar on said transducer for supporting said connection between said transducer coupling and said catheter, wherein said collar is slideably moveable between:

i) a first non-supporting position whereat said collar is adjacent said connection; and, ii) a second supporting position whereat said collar is disposed around said connection to provide support thereto; and d) wherein said collar comprises an elongate slot formed in said collar, said elongate slot having a closed proximal end; and, a pin attached to said transducer and extending into said elongate slot such that abutment of said pin against the proximal end of said elongate slot will limit movement of said collar in the distal direction.

8. The connector of claim 7 wherein said collar has a tapered internal bore, said tapered internal bore being configured relative to said catheter such that said collar will exert an increasingly strong grip on said catheter as said catheter is moved from said first position to said second position.

9. The connector of claim 7 wherein said collar has a countersink formed therein to facilitate movement from said first position to said second position.

10. The connector of claim 7 wherein said support member is configured to surround and support a proximal portion of said catheter when said catheter is coupled to said transducer.

11. The connector of claim 7 wherein said catheter coupling is threaded to said transducer coupling.

12. The connector of claim 7 wherein said collar has a plurality of open ended slots formed therein to define a plurality of gripping fingers, said gripping fingers being configured and positioned to firmly engage said catheter when said catheter is coupled to said transducer and when said collar is disposed in said second supporting position.

13. An ultrasound transducer, attachable to an ultrasound catheter having a catheter coupling said transducer comprising:

a hand held body;

b) a transducer element disposed within said body;

c) a bell attached to said transducer element extending through said body, a distal end of said bell defining a transducer coupling;

d) a collar slideably disposed upon said body to engage and support the catheter coupling, said collar having a non-supporting first position wherein said collar is disposed away from the catheter coupling and having a supporting second position wherein said collar is disposed around at least a portion of the catheter coupling, said collar having a non-supporting first position wherein said collar is disposed away from the catheter coupling and having a supporting second position wherein said collar is disposed around at least a portion of the catheter coupling, and wherein said collar comprises a plurality of open ended slots formed therein so as to define a plurality of gripping fingers, said gripping fingers firmly gripping the catheter coupling when said collar is disposed in the second position thereof.

14. The ultrasound transducer as recited in claim 13 wherein said collar further comprises:

(i) a close ended slot formed therein; and (ii) a pin rigidly attached to said ultrasound transducer, the pin extending through said slot, so as to limit the distal movement of said collar.

15. The ultrasound transducer as recited in claim 13 wherein said collar further comprises a tapered bore for receiving the catheter coupling, such that said tapered bore will exert a progressively tighter grip on the catheter coupling as said collar is moved from the first position thereof toward the second position thereof.

16. The ultrasound transducer as recited in claim 13 wherein said collar comprises a countersink formed therein for facilitating movement from the first position to the second position thereof.

17. An ultrasound transducer, attachable to an ultrasound catheter having a catheter coupling, said transducer comprising:

a) a hand held body;

b) a transducer element disposed within said body;

c) a bell attached to said transducer element extending through said body, a distal end of said bell defining a transducer coupling;

d) a collar slideably disposed upon said body to engage and support the catheter coupling, said collar having a non-supporting first position wherein said collar is disposed away from the catheter coupling and having a supporting second position wherein said collar is disposed around at least a portion of the catheter coupling, said collar having a non-supporting first position wherein said collar is disposed away from the catheter coupling and having a supporting second position wherein said collar is disposed around at least a portion of the catheter coupling, and wherein said collar comprises:

(i) a close ended slot formed therein; and (ii) a pin rigidly attached to the ultrasound transducer, the pin extending through said slot, so as to limit the distal movement of said collar.

18. The ultrasound transducer as recited in claim 17 wherein said collar comprises a tapered bore for receiving the catheter coupling, such that said tapered bore will exert a progressively tighter grip on the catheter coupling as said collar is moved from the first position thereof toward the second position thereof.

19. The ultrasound transducer as recited in claim 17 wherein said collar comprises a countersink formed therein for facilitating movement from the first position to the second position thereof.

20. An ultrasound transducer, attachable to an ultrasound catheter having a catheter coupling, said transducer comprising:

a) a hand held body;

b) a transducer element disposed within said body;

c) a bell attached to said transducer element extending through said body, a distal end of said bell defining a transducer coupling;

d) a collar slideably disposed upon said body to engage and support the catheter coupling, said collar having a non-supporting first position wherein said collar is disposed away from the catheter coupling and having a supporting second position wherein said collar is disposed around at least a portion of the catheter coupling, said collar having a non-supporting first position wherein said collar is disposed away from the catheter coupling and having a supporting second position wherein said collar is disposed around at least a portion of the catheter coupling and wherein said collar comprises a tapered bore for receiving the catheter coupling, such that said tapered bore will exert a progressively tighter grip on the catheter coupling as said collar is moved from the first position thereof toward the second position thereof.

21. The ultrasound transducer as recited in claim 20 wherein said collar comprises a countersink formed therein for facilitating movement from the first position to the second position thereof.

22. An ultrasound transducer attachable to an ultrasound catheter having a catheter coupling, said ultrasound transducer comprising:
   a) hand held body;
   b) a neck extending from said body;
   c) a transducer element disposed within said body;
   d) a boss extending from said neck;
   e) a bell attached to said transducer element and extending through said neck and said boss, said boss and said bell defining a transducer coupling;
   f) a collar slideably disposed around said neck, said collar having a non-supporting first position wherein said collar is retracted toward said body and having a supporting second position wherein said collar is extended so as to capture at least a portion of the catheter coupling, said collar comprising:
      i) a plurality of open ended slots formed therein so as to define a plurality of gripping fingers, said gripping fingers engaging the catheter coupling when said collar is disposed in the second position therein;
      ii) a close ended slot formed therein;
      iii) a tapered bore formed longitudinally therethrough for receiving the catheter coupling, said tapered bore more tightly gripping the catheter coupling as said collar is moved from the first position thereof toward the second position thereof;
      iv) a countersink formed at an entrance to said bore;
   g) a pin rigidly attached to said neck and extending into said close-ended slot so as to limit movement of said collar and to define the second position thereof; and
   h) wherein supporting of at least a portion of the catheter coupling mitigates the occurrence of ultrasound transmission member breakage by reducing mechanical stress applied to the proximal end thereof.

* * * * *